(12) United States Patent
Koenig et al.

(10) Patent No.: US 10,073,058 B2
(45) Date of Patent: Sep. 11, 2018

(54) DYNAMIC PULSED EDDY CURRENT PROBE

(71) Applicants: Kamalu Michael-Stanley Koenig, Centennial, CO (US); Owen Michael Malinowski, Gilbertsville, PA (US)

(72) Inventors: Kamalu Michael-Stanley Koenig, Centennial, CO (US); Owen Michael Malinowski, Gilbertsville, PA (US)

(73) Assignee: Structural Integrity Associates, San Jose, CA (US)

( * ) Notice: Subject to any disclaimer, the term of this patent is extended or adjusted under 35 U.S.C. 154(b) by 121 days.

(21) Appl. No.: 15/041,447

(22) Filed: Feb. 11, 2016

(65) Prior Publication Data

US 2016/0231282 A1    Aug. 11, 2016

Related U.S. Application Data

(60) Provisional application No. 62/114,934, filed on Feb. 11, 2015.

(51) Int. Cl.
*G01N 27/72* (2006.01)
*G01N 27/90* (2006.01)

(52) U.S. Cl.
CPC ....... *G01N 27/904* (2013.01); *G01N 27/9013* (2013.01)

(58) Field of Classification Search
CPC .............. G01N 27/904; G01N 27/902; G01N 27/9013; G01N 27/9053; G01N 27/90; G01N 27/9033; G01N 27/9046
USPC .......... 324/239, 238, 242, 262, 240; 73/643, 73/592, 622, 627
See application file for complete search history.

(56) References Cited

U.S. PATENT DOCUMENTS

| | | | |
|---|---|---|---|
| 3,229,197 A | 1/1966 | Renken, Jr. | |
| 3,840,802 A | 10/1974 | Anthony | |
| 3,932,813 A * | 1/1976 | Gallant | G01P 3/48 324/164 |
| 4,445,089 A * | 4/1984 | Harrison | G01N 27/9046 324/232 |
| 4,839,593 A | 6/1989 | Spies | |
| 4,843,319 A | 6/1989 | Lara | |
| 4,843,320 A | 6/1989 | Spies | |
| 4,929,898 A | 5/1990 | Spies | |
| 4,990,851 A | 2/1991 | Spies | |
| 5,399,968 A * | 3/1995 | Sheppard | G01N 27/902 324/232 |
| 5,446,382 A * | 8/1995 | Flora | G01N 27/902 324/232 |
| 5,491,409 A | 2/1996 | Flora et al. | |
| 5,659,248 A | 8/1997 | Hedengren et al. | |
| 5,670,878 A | 9/1997 | Katahara et al. | |
| 5,942,893 A * | 8/1999 | Terpay | G01N 27/9033 324/164 |
| 6,002,253 A | 12/1999 | Bornhofft et al. | |
| 6,037,768 A | 3/2000 | Moulder et al. | |

(Continued)

*Primary Examiner* — Thang Le
(74) *Attorney, Agent, or Firm* — Seth L. Hudson; Clements Bernard Walker, PLLC

(57) ABSTRACT

The present invention provides methods and systems for a dynamic pulsed eddy current probe that includes at least two magnetizing yokes having a first leg and a second leg, and a coil assembly comprising a coil, wherein the second leg of the at least two magnetizing yokes is positioned within the coil assembly.

20 Claims, 4 Drawing Sheets

(56) References Cited

U.S. PATENT DOCUMENTS

| | | | |
|---|---|---|---|
| 6,150,809 A | 11/2000 | Tiernan et al. | |
| 6,213,737 B1 | 4/2001 | Murakami et al. | |
| 6,275,030 B1 | 8/2001 | de Haan | |
| 6,291,992 B1 | 9/2001 | van Andel et al. | |
| 6,344,741 B1 | 2/2002 | Giguere et al. | |
| 6,593,737 B2 | 7/2003 | Crouzen et al. | |
| 6,720,775 B2 | 4/2004 | Plotnikov et al. | |
| 6,788,053 B2* | 9/2004 | Nekado | G01R 33/02 324/244 |
| 6,911,826 B2 | 6/2005 | Plotnikov et al. | |
| 7,154,265 B2 | 12/2006 | Togo et al. | |
| 7,250,757 B1* | 7/2007 | Tiernan | G01N 27/9046 324/228 |
| 7,952,348 B2 | 5/2011 | Sun et al. | |
| 8,390,280 B2 | 3/2013 | Badoux et al. | |
| 8,922,323 B2* | 12/2014 | Uozumi | H01F 1/24 29/602.1 |
| 2004/0245997 A1 | 12/2004 | Plotnikov et al. | |
| 2005/0068026 A1 | 3/2005 | May et al. | |
| 2007/0200563 A1* | 8/2007 | Daalmans | G01N 27/9006 324/237 |
| 2009/0121571 A1* | 5/2009 | Onuma | F04D 29/058 310/90.5 |
| 2010/0301851 A1* | 12/2010 | Park | B24B 49/105 324/240 |
| 2010/0315077 A1 | 12/2010 | De Haan et al. | |
| 2012/0274319 A1* | 11/2012 | Wincheski | G01R 33/12 324/239 |
| 2013/0009632 A1* | 1/2013 | Yamamoto | G01N 27/9046 324/222 |

\* cited by examiner

DYNAMIC PULSED EDDY CURRENT PROBE

CROSS REFERENCE TO RELATED PATENT APPLICATION

The present patent application/patent claims the benefit of priority of U.S. Provisional Patent Application No. 62/114,934, filed on Feb. 11, 2015, and entitled "DYNAMIC PULSED EDDY CURRENT PROBE," the contents of which are incorporated in full by reference herein.

FIELD OF THE INVENTION

The present invention relates generally to a dynamic pulsed eddy current probe, and more generally relates to a dynamic pulsed eddy current probe including at least two magnetizing yokes and a coil assembly.

BACKGROUND OF THE INVENTION

Eddy current inspection is a technique that can be used to determine the presence of flaws, such as cracks, in a specimen composed of conductive materials. Eddy current inspection utilizes electromagnetic induction, where a coil of a probe is placed proximate to a test specimen that is formed from conductive materials. The coil is energized via a current to create a magnetic field. The magnetic field induces eddy currents in the conductive materials of the test specimen, which generate a secondary magnetic field. The nature of the secondary magnetic field, such as its magnitude or directionality, at least partially depends on the structural features of the test specimen. For example, cracks, dents, or other structural irregularities may induce perturbations in the secondary magnetic field.

The prior art probes are circular in shape with a centrally located coil. The prior art probes do not allow simultaneous scanning and data acquisition on the specimens. Instead, these prior art devices require the probe to cease movement in order to acquire data on the specimen. The shape and design of the present invention overcomes this deficiency and allows the probe to simultaneously scan and acquire data on the specimen.

BRIEF SUMMARY OF THE INVENTION

According to an embodiment of the present invention, a dynamic pulsed eddy current probe that includes at least two magnetizing yokes having a first let and a second leg, a coil assembly comprising a coil, wherein the second leg of the at least two magnetizing yokes is positioned within the coil assembly.

According to another embodiment of the present invention, a dynamic pulsed eddy current probe that includes a magnetizing yoke having a top portion that connects the first leg and the second leg.

According to another embodiment of the present invention, a dynamic pulsed eddy current probe that includes a magnetizing yoke composed of ferrite.

According to yet another embodiment of the present invention, a dynamic pulsed eddy current probe that includes a coil composed of copper.

According to yet another embodiment of the present invention, a dynamic pulsed eddy current probe that includes a sensor array containing a plurality of simultaneously sampled magnetometers for detecting the secondary transient magnetic flux emanating from the conductive specimen.

According to yet another embodiment of the present invention, a dynamic pulsed eddy current probe that includes four magnetizing yokes.

According to yet another embodiment of the present invention, a dynamic pulsed eddy current probe that includes at least two magnetizing yokes containing a first leg and a second leg that are substantially circular.

According to yet another embodiment of the present invention, a dynamic pulsed eddy current probe that includes at least two substantially u-shaped magnetizing yokes having a first leg and a second leg, and a coil assembly including a coil, wherein the second leg of the at least two magnetizing yokes is positioned within the coil assembly.

According to yet another embodiment of the present invention, a dynamic pulsed eddy current probe that includes an opening within the coil assembly for receiving a sensor array.

According to yet another embodiment of the present invention, a dynamic pulsed eddy current probe that includes a single sensor array.

According to yet another embodiment of the present invention, a dynamic pulsed eddy current probe that includes a one-dimensional sensor array.

According to yet another embodiment of the present invention, a dynamic pulsed eddy current probe that includes a first magnetizing yoke, a second magnetizing yoke, a third magnetizing yoke, and a fourth magnetizing yoke with each yoke having a first leg and a second leg, a coil assembly including a coil, wherein the second leg of the first magnetizing yoke, the second magnetizing yoke, the third magnetizing yoke, and the fourth magnetizing yoke are positioned within the coil assembly.

According to yet another embodiment of the present invention, a dynamic pulsed eddy current probe that includes the magnetizing yokes arranged in pairs with the end of each pair in a spaced-apart relationship with the opposite pair.

According to yet another embodiment of the present invention, a dynamic pulsed eddy current probe that includes a sensor array including a plurality of simultaneously sampled magnetometers.

According to yet another embodiment of the present invention, a dynamic pulsed eddy current probe that includes a coil assembly including a first side, a second side, a third side, and a fourth side, whereby the second leg of the first magnetizing yoke is adjacent the first side, the second leg of the second magnetizing yoke is adjacent the second side, the second leg of the third magnetizing yoke is adjacent the third side, and the second leg of the fourth magnetizing yoke is adjacent the fourth side.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
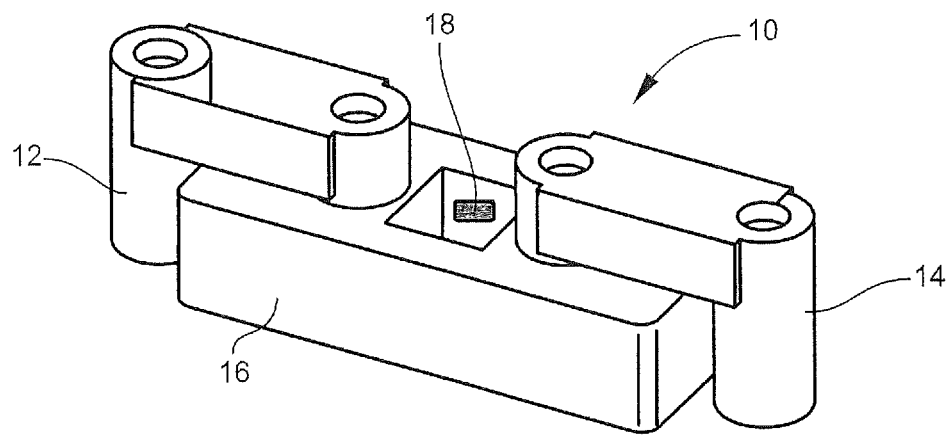
FIG. 1 is a perspective view of one embodiment of the present invention.

Referring now specifically to the drawings, an improved dynamic eddy current probe is illustrated in FIG. 1 and is shown generally at reference numeral 10. The probe 10 is generally designed for the nondestructive examination of electrically conductive materials using a dynamic pulsed eddy current technique while simultaneously scanning and acquiring data on the specimen. The probe 10 includes at least two magnetizing yokes—a first magnetizing yoke 12 and a second magnetizing yoke 14. A coil assembly 16 is positioned around a portion of the first magnetizing yoke 12 and second magnetizing yoke 14, and at least one sensor array 18 or other receiving element is disposed within an opening within the coil assembly 16.

Figure 2:
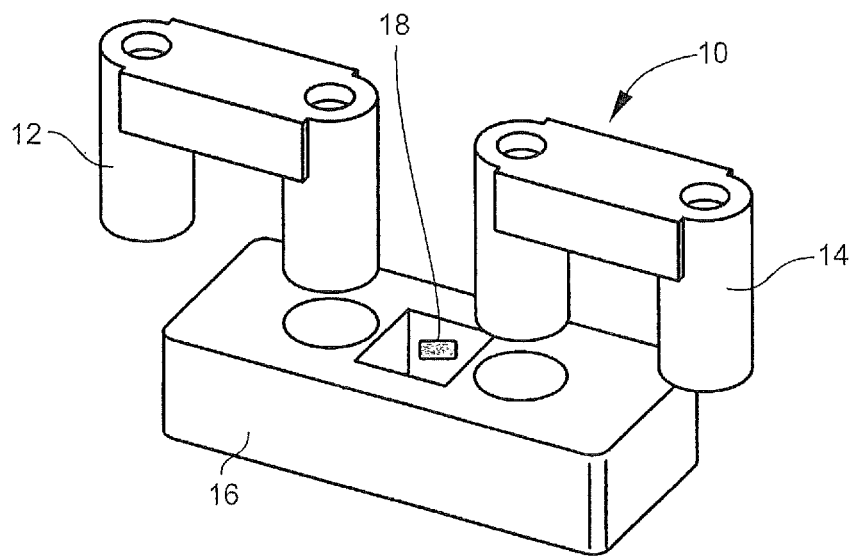
FIG. 2 is an exploded view of the embodiment of the present invention as shown in FIG. 1.

The first magnetizing yoke 12 and second magnetizing yoke 14, as shown in FIGS. 1 and 2, are substantially u-shaped. In other words, the magnetizing yokes 12, 14 have a first leg and a second leg that are connected by a top portion with each leg extending generally downwardly from the top portion. An interior cavity is formed between the inner sides of the first leg, second leg, and top portion. The first leg and top portion of the magnetizing yokes 12, 14 form substantially a portion of the exterior of the probe 10. In the exemplary embodiment of FIGS. 1 and 2, the probe 10 consists of the first magnetizing yoke 12 and the second magnetizing yoke 14 disposed in a spaced-apart relationship. The second leg of each magnetizing yoke 12, 14 is disposed adjacent each other and in a spaced-apart relationship.

The yokes 12, 14, as shown in FIGS. 1 and 2, have a generally cylindrical first leg and second leg having a first end, a second end, and an external surface. The top portion connects the second end of the first leg and the second end of the second leg. The top portion extends downwardly from the second end of the first leg and the second end of the second leg and continues partially along the external side of the first leg and second leg. The yokes 12, 14 also may contain a recessed bore disposed on the second end of the first leg and second end of the second leg. The recessed bore may also contain a shelf positioned therein. The recessed bore may be circular that corresponds with a circular shelf, as the recessed bore continues downwardly from the circular shelf.

The yokes 12, 14 are selectively secured to the coil assembly 16, wherein the second leg of the first yoke 12 and the second leg of the second yoke 14 are engaged to the coil assembly 16. The coil assembly 16 contains a pair of positioning bores for receiving the second leg of the first yoke 12 and the second leg of the second yoke 14. The second leg of the first yoke 12 and the second leg of the second yoke 14 may be engaged within the positioning bores or selectively secured within the positioning bores. The positioning bores correspond to the shape of the second leg of the yokes 12, 14. As illustrated in FIGS. 1 and 2, the positioning bores are circular to correspond with the circular second leg of the yokes 12, 14, wherein the diameter of the positioning bore is slightly larger than the diameter of the second leg of the yokes 12, 14.

The coil 16 is positioned within the inner cavity of the probe 10 and adjacent the interior side of the first leg and the second leg of the magnetizing yokes 12, 14. The coil 16, as shown in FIG. 2, is positioned within the cavity of the two magnetizing yokes 12, 14 and disposed adjacent the interior side of the second leg of each magnetizing yoke 12 14. The coil 16 is continuous and partially encircles the second leg of the first magnetizing yoke 12 and the second leg of the second magnetizing yoke 14 and engaging the first magnetizing yoke 12 to the second magnetizing yoke 14. The coil 16, driven by a current pulse, subsequently generates and transmits a primary transient magnetic field that induces transient eddy currents into the conductive specimen. These transient eddy currents generate a secondary transient magnetic field within the conductive specimen.

The at least one sensor array 18 may be positioned within an opening in the coil assembly 16. As shown in FIGS. 1 and 2, the at least one sensor array 18 is disposed near the exterior sides of the second leg of the first magnetizing yoke 12 and the second magnetizing yoke 14. As illustrated, an opening is formed within the coil assembly 16 for allowing a single sensor array 18 to be disposed within the opening of the coil assembly 16. In this arrangement, the second leg of the first magnetizing yoke 12 and the second leg of the second magnetizing yoke 14 provide a shielding effect for shielding the sensor array 18 from the field. The sensor array 18 is oriented with its sensitive axis normal or parallel to the surface of the conductive specimen on which the probe is placed and tasked to analyze.

In one embodiment, the sensor array 18 contains a plurality of simultaneously sampled magnetometers for detecting the secondary transient magnetic flux emanating from the conductive specimen. As illustrated in FIGS. 1 and 2, the sensor array 18 is a one-dimensional sensor array. However, additional sensor arrays 18 may be disposed within the probe 10 for creating a two-dimensional or three-dimensional sensor array.

In a scanning pulsed eddy current application, there are two sources of eddy currents within the electrically conductive specimen: transient eddy currents induced by the primary transient magnetic field and eddy currents induced by the motion of the probe. The eddy currents induced by motion will produce perturbations on the secondary transient magnetic field. These perturbations could be detected as false positives by the scanning probe. The value of the magnetic Reynolds of the probe determines which eddy current induction mechanism dominates. A minimal magnetic Reynolds number restricts the extent to which eddy currents due to the motion of the probe are generated. The probe 10 was designed to minimize its magnetic Reynolds number with a shorter length in the scanning direction. This ensures that the signal measured by the probe 10 while scanning is dominated by the secondary transient magnetic field and that the eddy currents induced by the motion of probe 10 have little to no influence on the received signal. The shorter dimension in the scanning direction allows the probe 10 to simultaneously scan and acquire data on the specimen. In addition, the shorter dimension results in a lower sensor-lift-off when scanning a pipe from the ID surface with the long axis of the probe 10 in the pipe's axial direction. The magnetizing yokes 12, 14 may be constructed of ferrite to further concentrate the magnetic field of the coil.

In an alternative embodiment, the probe 110 includes a first magnetizing yoke 112, a second magnetizing yoke 114, a third magnetizing yoke 116, and a fourth magnetizing yoke 118. A coil assembly 120 is positioned around a portion of the first magnetizing yoke 112, the second magnetizing yoke 114, the third magnetizing yoke 116, and the fourth magnetizing yoke 118, and at least one sensor array 122 is disposed within the coil assembly 120.

Figure 3:
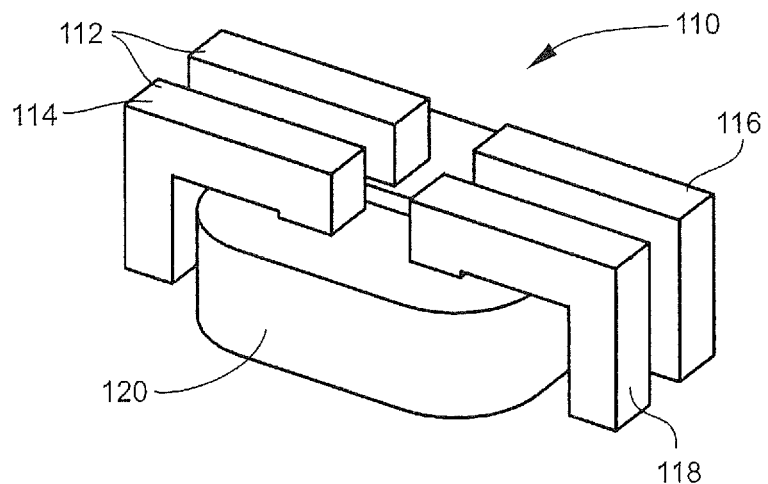
FIG. 3 is a perspective view of another embodiment of the present invention.

The magnetizing yokes 112, 114, 116, and 118, as shown in FIG. 3, are substantially u-shaped as described above. The first leg and top portion of the magnetizing yokes 112, 114, 116, and 118 form substantially a portion of the exterior of the probe 110. In the exemplary embodiment of FIGS. 3 and 4, the probe 110 consist of first magnetizing yoke 112 and second magnetizing yoke 114 disposed in a spaced-apart side-by-side relationship. The third magnetizing yoke 116 and fourth magnetizing yoke 118 are disposed within a spaced-apart side-by-side relationship.

The magnetizing yokes 112, 114, 116, and 118 contain a first leg and a second leg. The second leg of the first magnetizing yoke 112 is disposed adjacent the second leg of the third magnetizing yoke 116, and the second leg of the second magnetizing yoke 114 is disposed adjacent the second leg of the fourth magnetizing yoke 118. The second let of the magnetizing yokes 112, 114, 116, and 118 are partially positioned within the coil assembly 120.

The coil assembly 120 is positioned within the inner cavity of the probe 10 formed between the first and second legs of the magnetizing yokes 112, 114, 116, and 118. The coil assembly 120 is adjacent the interior side of the first leg and second leg of the magnetizing yokes 112, 114, 116, 118. A coil, preferably composed of copper, is housed within the coil assembly 120.

Figure 4:
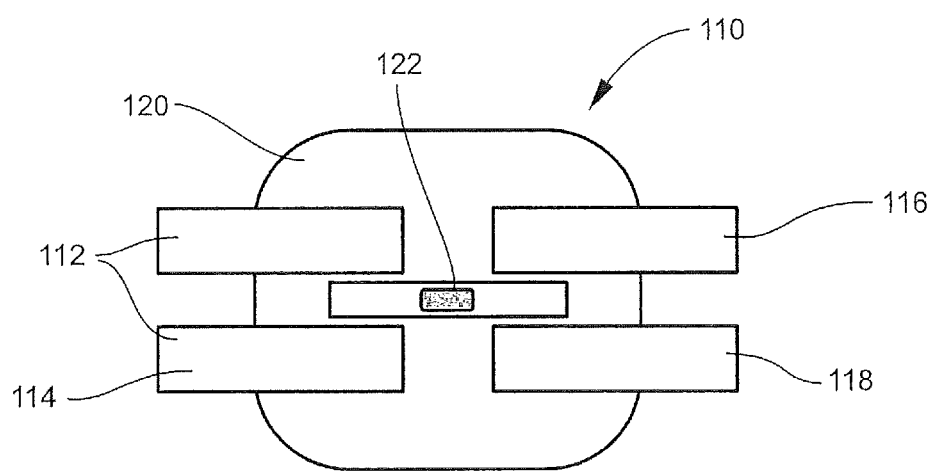
FIG. 4 is a top view of the embodiment of the present invention as shown in FIG. 3.

The at least one sensor array 122 is disposed within the coil assembly 120. As shown in FIG. 4, the at least one sensor array 122 is centrally located within the coil assembly 120 and disposed adjacent the exterior sides of the second leg of the magnetizing yokes 112, 114, 116, and 118. As illustrated, an opening is formed within the coil assembly 120 for allowing a single sensor array 122 to be disposed within the opening of the coil 120. As illustrated in FIG. 4, the sensor array 122 is a one-dimensional sensor array. However, additional sensor arrays 122 may be disposed within the probe 110 for creating a two-dimensional or three-dimensional sensor array.

Figure 5:
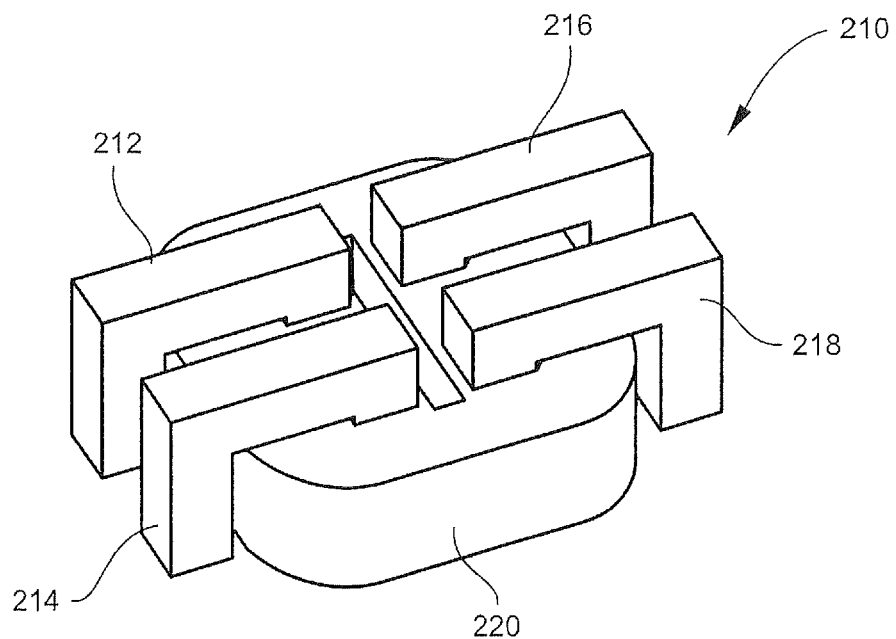
FIG. 5 is a perspective view of another alternative embodiment of the present invention.
Figure 6:
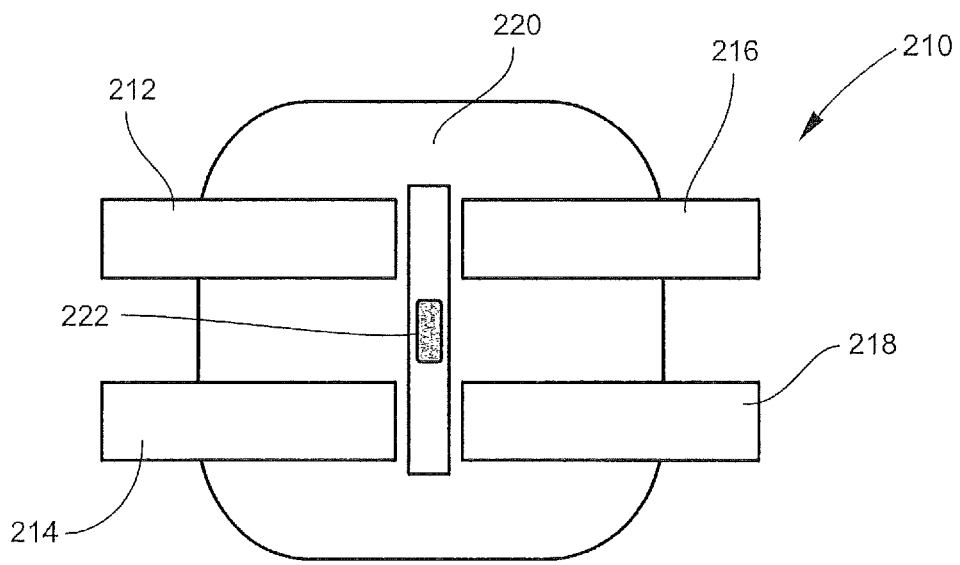
FIG. 6 is a top view of the embodiment of the present invention as shown in FIG. 5.

Another alternative embodiment is illustrated in FIGS. 5 and 6. In this embodiment, the magnetizing yokes 212, 214, 216, and 218 and coil assembly 220 are similar to that of the embodiment shown in FIGS. 3 and 4. However, the opening for receiving the sensory array 222 is disposed in the longitudinal direction, which is rotated 90° from the arrangement of the cavity as shown in FIGS. 3 and 4 that illustrate a cavity spanning the axial direction.

Figure 7:
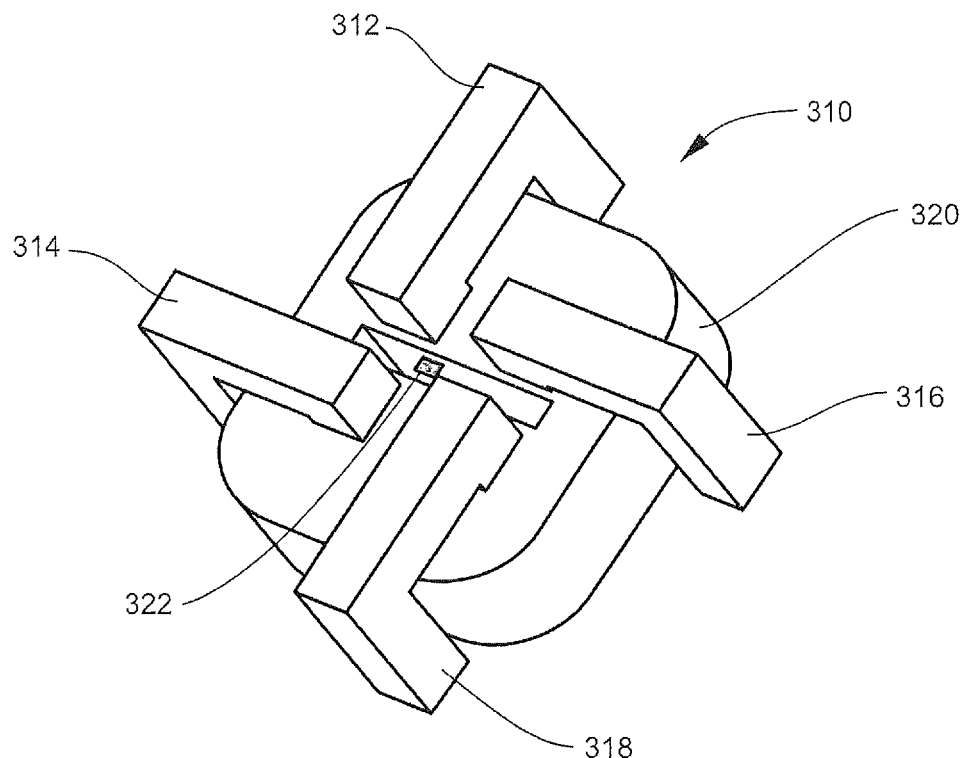
FIG. 7 is a perspective view of another alternative embodiment of the present invention.
Figure 8:
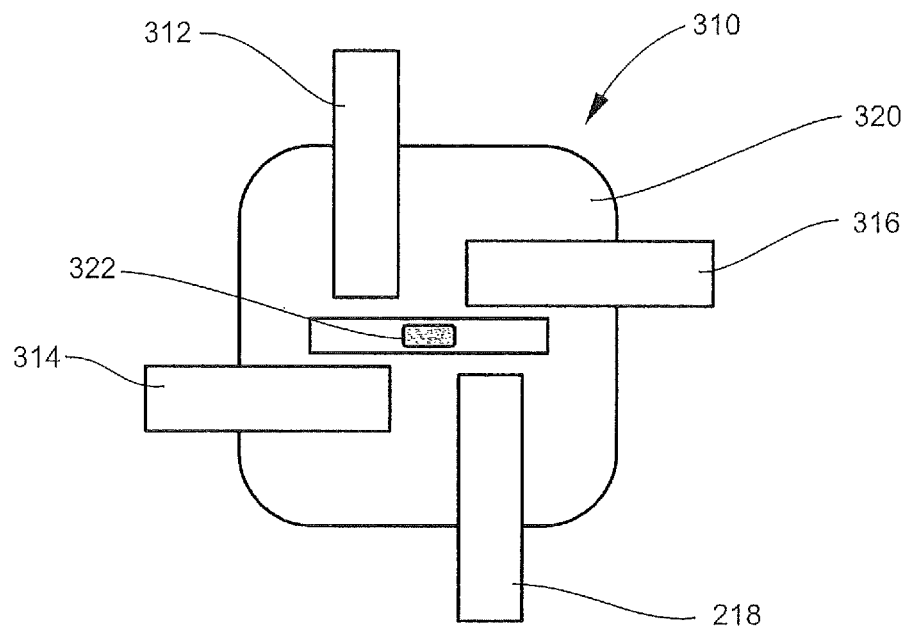
FIG. 8 is a top view of the embodiment of the present invention as shown in FIG. 7.

Another alternative embodiment is illustrated in FIGS. 7 and 8. In this embodiment, the magnetizing yokes 312, 314, 316, and 318 are positioned around separate sides of the coil assembly 320. The coil assembly has a first side, a second side, a third side, and a fourth side. The second leg of the each magnetizing yoke 312, 314, 316, 318 is partially positioned within the coil assembly 320. The first leg of each magnetizing yoke 312, 314, 316, 318 is positioned adjacent a separate side of the coil assembly 320. The first leg of the first magnetizing yoke 312 is positioned adjacent the first side of the coil assembly 320. The first leg of the second magnetizing yoke 314 is positioned adjacent the second side of the coil assembly 320. The first leg of the third magnetizing yoke 316 is positioned adjacent the third side of the coil assembly 320. The first leg of the fourth magnetizing yoke 312 is positioned adjacent the fourth side of the coil assembly 320. An opening is disposed between the first legs of the magnetizing yokes 312, 314, 316, 318 for housing a sensor array 322.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A dynamic pulsed eddy current probe, comprising:
a first magnetizing yoke having a first leg and a second leg and a second magnetizing yoke having a first leg and a second leg with each leg having an interior side and an exterior side;
a cavity formed within the interior side of the second leg and the first leg of the first magnetizing yoke and the interior side of the second leg and the first leg of the second magnetizing yoke; and
a coil assembly comprising a coil positioned within the cavity and a pair of positioning bores, wherein the second leg of each of the at least two magnetizing yokes is positioned within the pair of positioning bores of the coil assembly.

2. The dynamic pulsed eddy current probe according to claim 1, wherein the magnetizing yokes comprise a top portion connecting the first leg and the second leg.

3. The dynamic pulsed eddy current probe according to claim 1, wherein the magnetizing yoke is composed of ferrite.

4. The dynamic pulsed eddy current probe according to claim 1, wherein the coil is composed of copper.

5. The dynamic pulsed eddy current probe according to claim 1, further comprising an opening within the coil assembly for receiving a sensor array.

6. The dynamic pulsed eddy current probe according to claim 1, further comprising a sensor array.

7. The dynamic pulsed eddy current probe according to claim 1, further comprising a sensor array that contains a plurality of simultaneously sampled magnetometers for detecting the secondary transient magnetic flux emanating from the conductive specimen.

8. The dynamic pulsed eddy current probe according to claim 1, further comprising four magnetizing yokes.

9. The dynamic pulsed eddy current probe according to claim 1, wherein the at least two magnetizing yokes contain a first leg and a second leg that are substantially circular.

10. A dynamic pulsed eddy current probe, comprising:
at least two magnetizing yokes having a first leg and a second leg, wherein each leg has an exterior side and an interior side, the first leg and second leg are connected by a top portion with each leg extending generally downward from the top portion and a cavity is formed between the interior sides of the first leg and the second leg; and
a coil assembly comprising a coil positioned within the cavity and disposed adjacent the interior side of the second leg of each magnetizing yoke and a pair of positioning bores, wherein the second leg of each of the at least two magnetizing yokes is positioned within the pair of positioning bores of the coil assembly.

11. The dynamic pulsed eddy current probe according to claim 10, further comprising an opening within the coil assembly for receiving a sensor array.

12. The dynamic pulsed eddy current probe according to claim 10, further comprising a single sensor array.

13. The dynamic pulsed eddy current probe according to claim 10, further comprising a one-dimensional sensor array.

14. A dynamic pulsed eddy current probe, comprising:
a first magnetizing yoke, a second magnetizing yoke, a third magnetizing yoke, and a fourth magnetizing yoke each having a first leg and a second leg having an interior side;
a cavity;
a coil assembly comprising a coil disposed adjacent the interior side of the second leg of the first magnetizing yoke, the interior side of the second magnetizing yoke, the interior side of the third magnetizing yoke, and the interior side of the fourth magnetizing yoke;
and positioning bores disposed within the cavity, wherein the second leg of the first magnetizing yoke, the second magnetizing yoke, the third magnetizing yoke, and the fourth magnetizing yoke are positioned within the positioning bores of the coil assembly.

15. The dynamic pulsed eddy current probe according to claim 14, wherein the magnetizing yokes are arranged in pairs with the end of each pair in a spaced-apart relationship with the opposite pair.

16. The dynamic pulsed eddy current probe according to claim 14, further comprising an opening within the coil assembly.

17. The dynamic pulsed eddy current probe according to claim 14, further comprising a sensor array that comprises a plurality of simultaneously sampled magnetometers.

18. The dynamic pulsed eddy current probe according to claim 14, wherein the coil assembly comprises a first side, a second side, a third side, and a fourth side, whereby the second leg of the first magnetizing yoke is adjacent the first side, the second leg of the second magnetizing yoke is adjacent the second side, the second leg of the third magnetizing yoke is adjacent the third side, and the second leg of the fourth magnetizing yoke is adjacent the fourth side.

19. The dynamic pulsed eddy current probe according to claim 14, wherein the magnetizing yokes are composed of ferrite.

20. The dynamic pulsed eddy current probe according to claim 14, wherein the coil assembly comprises a housing that contains a coil within.

* * * * *

UNITED STATES PATENT AND TRADEMARK OFFICE
CERTIFICATE OF CORRECTION

PATENT NO. : 10,073,058 B2  
APPLICATION NO. : 15/041447  
DATED : September 11, 2018  
INVENTOR(S) : Koenig et al.

Page 1 of 1

It is certified that error appears in the above-identified patent and that said Letters Patent is hereby corrected as shown below:

On the Title Page

Column 1, item (60) Related U.S. Application Data:  
Change "Provisional application No. 62/114,934, filed on Feb. 11, 2015" to This application claims the benefit of Provisional application No. 62/114,934, filed on Feb. 11, 2015.

Signed and Sealed this  
Thirtieth Day of October, 2018

Andrei Iancu  
*Director of the United States Patent and Trademark Office*